United States Patent
Srivastava et al.

(12)

(10) Patent No.: US 6,610,705 B1
(45) Date of Patent: Aug. 26, 2003

(54) PROCESS FOR THE PREPARATION OF DIARYL NAPHTHYL METHANES

(75) Inventors: Neeta Srivastava, Lucknow-1 (IN); Arvinder Grover, Lucknow-1 (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/539,790

(22) Filed: Mar. 31, 2000

(51) Int. Cl.⁷ .................. A61K 31/445; C07D 211/06
(52) U.S. Cl. ................. 514/319; 514/212; 514/428; 514/651; 546/205; 548/576; 556/466; 564/347; 564/352; 568/631; 568/665; 568/667; 568/809
(58) Field of Search ................. 514/212, 319, 514/428, 651; 546/205; 548/576; 556/466; 564/347, 352; 568/631, 665, 667, 809

(56) References Cited

U.S. PATENT DOCUMENTS

| | | | | |
|---|---|---|---|---|
| 4,230,862 A | * | 10/1980 | Suarez et al. | 546/237 |
| 4,351,844 A | * | 9/1982 | Patchett et al. | 424/279 |
| 4,707,464 A | * | 11/1987 | Takashima et al. | 503/216 |
| 5,691,353 A | * | 11/1997 | Bryant et al. | 514/319 |
| 5,811,421 A | * | 9/1998 | Dpdge et al. | 514/212 |
| 5,952,350 A | * | 9/1999 | Cullinan et al. | 514/319 |

OTHER PUBLICATIONS

Cervinka et al. "Asymmetric reactions . . . " CA 67:63903 (1967).*
Gabard et al. "Synthesis of some substituted tetralins" CA 60:52581 (1964).*
Johnson et al. "Ring acylation of phenols" CA 85:192377 (1976).*
Franz et al. "Origin of certain heterocyclic compounds form . . . " CA 87:604061 (1977).*
Casiraghi et al. "Chiral novolacs. Enanticontroled synthesis . . . " CA 102:7120 (1984).*
Johnston et al. "Electron transfer reactions . . . " CA 112:54905 (1990).*
Inomata et al. "Radiation sensitive resin composition . . . " CA 121:267848 (1994).*
Parke, Davis Co. "Amino diols" CA 47:19235.*
Miyai et al "Novel reductive Friedel crafts alkylation . . . " CA 130:237317 (1999).*

* cited by examiner

*Primary Examiner*—Ceila Chang
(74) *Attorney, Agent, or Firm*—Birch, Stewart, Kolasch & Birch, LLP

(57) ABSTRACT

The invention relates to novel diaryl naphthyl methane compounds having general formula I as shown herein below, and said compounds useful in the treatment of esterogen related disease or syndrome,

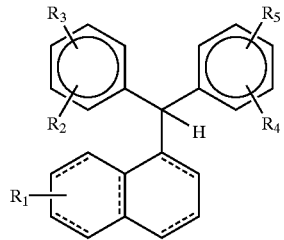

Formula I Pharmaceutical compositions comprising said novel methane derivatives, process for the preparation of the novel methane derivatives and methods for the treatment of esterogen related diseases or syndrome.

23 Claims, No Drawings

PROCESS FOR THE PREPARATION OF DIARYL NAPHTHYL METHANES

FIELD OF THE INVENTION

This invention relates to diaryl naphthyl methanes and a process for preparation of said methane derivatives. The present invention particularly relates to a process or preparation of substituted secondary and tertiary amino alkoxy diaryl naphthyl methane derivatives, preparation of pharmaceutical composition containing such compounds as active ingredients and their use as contraceptives, in the treatment and prophylaxes of breast cancer, osteoporosis, hypercholesteremia, endometriosis, vasoconstriction, endometrial disorders and in estrogen replacement therapy (ERT).

BACKGROUND OF THE INVENTION

Estrogen agonists as well as antagonists act through their interaction with estrogen receptor. This estrogen receptor protein has an active site where the ligand binds. It has been visualized as composed of two units, one having a shape complimentary to the structure of estradiol where estradiol finds a proper fit for producing estrogen agonistic activity. The second site provides binding of structural unit such as a substituted amino alkoxy aryl group thereby causing interference with the initiation of the hormonal activity as observed with estrogen antagonists. Based on this visualization, estrogen receptor model has been proposed easier. This present work utilizes the receptor model towards designing of novel estrogen antagonists.

OBJECTS OF THE INVENTION

The main object of the invention is to provide novel diarylnaphthyl methane compounds having structural Formula 1 and their derivatives, useful in the treatment of estrogen related diseases such as breast cancer, osteoporosis, hypercholesteremia, endometriosis, vasoconstriction, endometrial disorders and in estrogen replacement therapy (ERT).

Another object is to provide pharmaceutical compositions containing the novel diarylnaphthyl methane compounds having structural formula 1.

Yet another object is to provide methods for the preparation of novel diarylnapththyl methane compounds and their derivatives.

SUMMARY OF THE INVENTION

In accordance with the above and other objectives, the invention provides novel substituted diaryl naphthyl methane compounds having structural formula 1 and its derivatives, being a novel group of non-steroidal compounds and exhibiting estrogenic, antiestrogenic and contraceptive activities. The invention also provides methods for the preparation of the said novel diaryl naphthyl methane compounds and their derivatives. The invention also provides pharmaceutical compositions containing said novel diary naphthyl methane compounds and their derivatives.

DETAILED DESCRIPTION OF THE INVENTION

Accordingly the invention provides novel diaryl naphthyl methane compounds having general formula 1 as shown herein below,

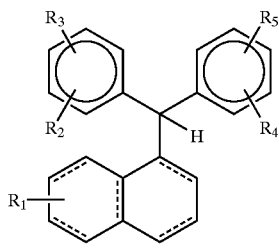

Formula I wherein, $R_1$, $R_2$, $R_3$, $R_4$, $R_5$ represent H, OH, lower alkyl, lower alkoxy group having straight or branched chain radical containing 1–6 carbon atoms selected from methyl, ethyl, n-propyl, isopropyl, n-butyl, tertiary butyl, n-amyl, n-hexyl, 2-ethyl butyl in case of lower alkyl and also as the alkyl residue constituting the lower alkoxy group, substituted alkoxy groups, epoxy alkoxy, alkyl/dialkyl amino alkoxy, cyclic alkyl amino alkoxy, the dotted indicate 1,2,3,4-tetrahydro naphthyl ring or 5,6,7,8-tetrahydronaphthyl ring, said compounds exhibiting estrogenic, antiestrogenic and contraceptive activities.

Substituted diaryl naphthyl methane derivatives, a novel group of non-steroidal compounds is showing promising estrogenic, antiestrogenic and contraceptive activities. The hormonal profile of such compounds is suitable for the treatment and prophylaxes of breast cancer, osteoporosis, hypercholesteremia, endometriosis, vasoconstriction, endometrial disorders and in estrogen replacement therapy.

The invention provides a novel substituted aminoalkoxy diaryl naphthyl methane derivatives thereof, represented by general formula 1 as shown hereinbelow:

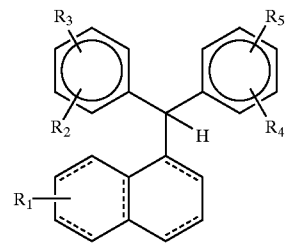

Wherein $R_1$, $R_2$, $R_3$, $R_4$, $R_5$ are H, OH, lower alkyl, a substituted lower alkoxy group having a straight or branched chain radical containing 1–6 carbon atoms, for example methyl, ethyl, n-propyl, isopropyl, n-butyl, tertiary butyl, n-amyl, n-hexyl, 2-ethyl butyl in case of lower alkyl and also as the alkyl residue constituting the lower alkoxy group. Substituent on the alkyl chain of alkoxy radical can be H or OH, a substituted amino lower alkoxy group wherein the lower alkoxy substituent is as defined above, the substituent on the nitrogen atom is H, or a lower alkyl radical as defined above or constitutes a cyclic polymethylene system containing nitrogen atom, i.e. $N(CH_2)_n$ wherein n=2–8. The naphthyl residue can be a substituted naphthyl, substituted 1,2,3,4-tetrahydronaphthyl or a substituted 5,6,7,8-tetrahydronaphthyl.

The compounds synthesized were tested for estrogenic, antiestrogenic activies in rats. A number of these compounds showed percent prevention of pregnancy at doses 10 mg per kg or below when administered orally to female albino rats on days 1–7 p.c. or on single day schedule.

The most preferred compounds, represented by formula 1 are given below:

1. (4-Methoxyphenyl)-(4-pyrrolidinoethoxyphenyl)-naphth-1-yl-methane HCl
2. (4-Methoxyphenyl)-(4-piperidinoethoxyphenyl)-naphth-1-yl-methane
3. (4-Methoxyphenyl)-(3-methyl4-piperidinoethoxyphenyl)-naphth-1-yl-methane
4. (4-Methoxyphenyl)-(4-pyrrolidinoethoxyphenyl)-1,2,3,4-tetrahydro-naphth-1-yl-methane
5. (4-Methoxyphenyl)-(4-pyrrolidinoethoxyphenyl)-5,6,7,8-tetrahydro-naphth-1-yl-methane HCl
6. (4-Methoxyphenyl)-(4-(2-hydroxy-3-cyclopropylamino)-propoxy)-phenyl-naphth-1-yl-methane
7. (4-Methoxyphenyl)-(4-(2-hydroxy-3-n-butylaminopropoxy)phenyl)-1,2,3,4-tetrahydronaphth-1-yl-methane The most preferred compounds belonging to the class of diary naphthyl methanes represented by formula Ia are given below:

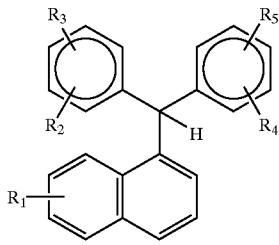

Formula Ia 1. (4-Methoxyphenyl)-(4-pyrrolidinoethoxyphenyl)-naphth1-yl-methane HCl
2. (4-Methoxyphenyl)-(4-piperidinoethoxyphenyl)-naphth-1-yl-methane
3. (4-Methoxyphenyl)-(3-methyl-piperidinoethoxyphenyl)-naphth-1-yl-methane The invention includes within the scope partially reduced substituted naphthalene residue to provide derivatives of substituted diaryl 1,2,3,4-tetrahydro naphthyl methane represented by the general formula Ib wherein $R_1$, $R_2$, $R_3$, $R_4$, $R_5$, have the meaning as stated above.

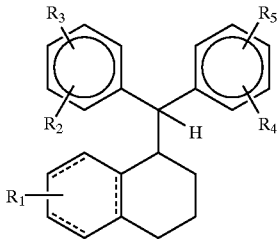

Formula-Ib

Preferred compounds belonging to Ib are:
1. (4-Methoxyphenyl)-(4-piperidinoethoxyphenyl)-1,2,3,4-tetrahydronapth-1-yl-methane.
2. (4-methoxyphenyl)-(3-methyl-4-piperidinoethoxyphenyl)-1,2,3,4-tetrahydronaphth-1-yl-methane. 3. (4-Methoxyphenyl)-(4-(2-hydroxy-3-n-dibutylaminopropoxy)phenyl-1,2,3,4-tetrahydronaphth-1-yl-methane.

In yet another modification included within the scope are the partially reduced naphthalene residue containing derivatives of substituted diaryl 5,6,7,8-tetrahydro naphthyl methane represented by the general formula Ic.

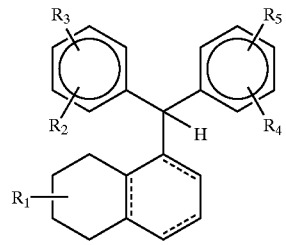

Formula Ic wherein $R_1$, $R_2$, $R_3$, $R_4$, $R_5$ have the meanings as stated above.

Preferred compounds of Ic are:
1. (4-Methoxyphenyl)-(4-pyrrolidinoethoxyphenyl)-5,6,7,8-tetrahydronaphth-1-yl-methane hydrochloride.
2. (4-Methoxyphenyl)-(4-N,N-diethylaminoethoxyphenyl)-5,6,7,8-tetrahydro-naphth-1-yl-methane.

The preparation of compounds shown in formula 1, wherein $R_1$, $R_2$, $R_3$, $R_4$, $R_5$ are as defined above is described hereinbelow. The process comprises the steps of conducting Friedel-Crafts reaction of substituted α-naphthoic acid with the substituted phenol in the presence of Lewis acid to give a naphthophenone derivative which is reduced by a metal hydride in a protic solvent to the corresponding alcohol which is subjected to a second Friedel-Crafts reaction with a phenol derivative in the presence of a Lewis acid under low temperature to produce compound of formula 1 wherein one of the substituent $R_1$, $R_2$, $R_3$, $R_4$, $R_5$ is a hydroxy group which is reacted with a tertiary amino alkyl chloride to produce corresponding tertiary amino alkoxy compound or alternatively treated with epichlorohydrin under basic condition either neat or in organic solvent such as acetone, DMSO to produce corresponding 2,3-epoxy-propyloxy derivatives which on treatment with an amine produce hydroxy substituted corresponding secondary amino alkoxy derivatives.

PHARMACEUTICAL COMPOSITION

Typical composition includes a compound of formula 1 or a pharmaceutically acceptable acid addition salt thereof, associated with a pharmaceutically acceptable excipient which may be a carrier or a diluents or be diluted or be diluted by a carrier or enclosed within a carrier which can be in the form of a capsule, sachet, paper or other container. In making the composition, conventional techniques for the preparation of pharmaceutical composition may be used for example the active compound will usually be mixed with a carrier, or diluted by a carrier, enclosed within a container, which may be in the form of an ampoule, capsule, sachet paper or other container. When the carrier serves as a diluent, it may be solid, semi-solid or liquid material which act as a vehicle, excipient, or medium of the active compound. The active compound can be adsorbed on a granular solid. Some examples of suitable carriers are water, salt solution, alcohol, polyethyleneglycol, polyhydroxyethoxylated castor oil, gelatine, lactose, amylase, magnesium stearate, talc, silicic acid, fatty acid monoglycerides and diglycerides, pentaerythritol fatty acid esters, hydroxymethylcellulose and polyvinylpyrrolidene. The formulation may also include wetting agents, emulsifying and suspending agents, preserving agents, sweetening agents or flavouring agents. The formulations of the invention may be formulated so as to provide quick, sustained, or delayed release of the active ingredient after administration to %he patient by employing procedures well known in the art.

The pharmaceutical preparations can be sterilized and mixed, if desired, with auxiliary agents, emulsifiers, salt for influencing osmotic pressure, buffers and/or colouring substances and the like, which do not deleteriously react with the active compounds.

For parenteral application, particularly suitable are injectable solutions or suspensions, preferably aqueous solutions with the active compounds dissolved in polyhydroxylated castor oil.

Tablets, dragees, or capsules having talc and/or a carbohydrate carrier or binder or the like are particularly suitable for oral application. Preferable carriers for tablets, dragees, or capsules include lactose, corn starch, and/or potato starch. A syrup or elixir can be used in cases where a sweetened vehicle can be employed.

The compound according to this invention may be suitable for administration to an animal. Such animals include both domestic animals, for example livestock, laboratory animals, and household pets, and non-domestic animals such as wildlife. More preferably, the animal is a vertebrate. Most preferably a compound according to this invention shall be administrated to a mammal. It is especially preferred that the animal is a domestic animal or a human. The most preferred mammal is a human. For such purposes, a compound of this invention may be administrated as a feed additive or in bulk form.

The preparation of the novel compounds and its derivatives are described in the following non-imitative examples.

Novel diaryl naphthyl methanes of formula I have been prepared

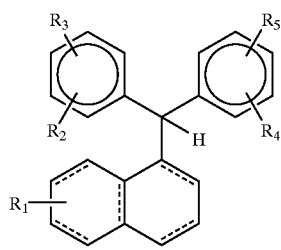

Accordingly the present invention provides novel diaryl naphthyl methanes and a process for the preparation of said methane compounds of general formula I useful in the treatment of estrogen related disease or syndrome wherein $R_1$, $R_2$, $R_3$, $R_4$, $R_5$ are (H, OH, lower alkyl, lower alkoxy group having straight or branched chain radical containing 1–6 carbon atoms such as methyl, ethyl, n-propyl, isopropyl, n-butyl, tertiary butyl, n-amyl, n-hexyl, 2-ethyl butyl in case of lower alkyl and also as the alkyl residue constituting the lower alkoxy group, substituted alkoxy groups, epoxy alkoxy, alkyl/dialkyl amino alkoxy, cyclic alkyl aminoalkoxy, hydroxy substituted alkyl/dialkyl/cyclic alkyl aminoalkoxy, the dotted lines indicate 1,2,3,4-tetrahydro naphthyl ring or 5,6,7,8-tetrahydronaphthyl ring, which comprises (i) reacting a compound of formula II wherein

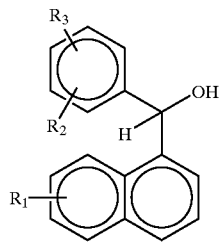

Formula II $R_1$, $R_2$ and $R_3$ is H, OH, alkyl or alkoxy as stated above with phenolic compound under the conventional. Friedel Crafts reaction conditions to produce the compound of Formula I wherein $R_1$, $R_2$, $R_3$, $R_4$ is H, OH, alkyl or alkoxy as stated above and $R_5$ is OH dotted lines indicate the presence of double bonds (ii) optionally subjecting the compound of formula I as obtained above in step (I) to the conventional hydrogenation conditions to give the tetrahydronaphthyl compound of formula I wherein dotted lines in one ring of the naphthyl group show the presence of double bonds; (iii) reacting compound of formula I wherein $R_1$, $R_2$, $R_3$, $R_4$ are as stated above in step (I), $R_5$ is OH with an alkylating agent in the presence of a base at a temperature in the range 300 to 120° C. for a period in the range of 1–12 hrs and recovering the alkylated product of formula I wherein $R_5$ is alkoxy, epoxy alkoxy, alkyl or dialkyl amino alkoxy, cyclic alkyl aminoalkoxy, cyclic alkyl amino alkoxy, $R_1$, $R_2$, $R_3$ and $R_4$ are as stated above in step (I), (iv) reacting compound of formula I wherein $R_5$ is epoxy alkoxy with an amine at a temperature in the range of 30 to 120° C. for a period in the range of 1 to 12 hr and recovering the compound of formula I wherein $R_1$, $R_2$, $R_3$, $R_4$ are as stated above in step (I) and $R_5$ is hydroxy substituted alkyl/dialkyl/cyclic alkyl amino alkoxy group, converting the amino compounds of formula I to their salts by known methods.

DESCRIPTION OF PREFERRED EMBODIMENTS

Novel compounds of general formula 1

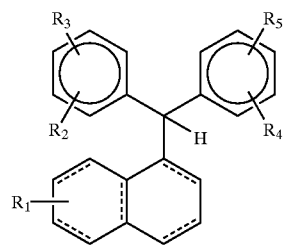

wherein the preferred compounds are represented below
1. (4-Methoxyphenyl)-(4-pyrrolidinoethoxyphen-yl-methane HCl
2. (4-Methoxyphenyl)-(4-piperidinoethoxyphenyl)-naphth-1-yl-methane
3. (4-Methoxyphenyl)-(3-methyl-4-piperidinoethoxyphenyl-naphth-1-yl-methane
4. (4-Methoxyphenyl)-(4-pyrrolidinoethoxyphenyl)-1,2,3,4-tetrahydro-naphth-1-yl-methane
5. (4-Methoxyphenyl)-(4-pyrrolidinoethoxyphenyl)-5,6,7,8-tetrahydro-naphth-1-yl-methane HCl
6. (4-Methoxyphenyl)-(4-2-hydroxy-3-cyclopropylamino)-propoxy)-phenyl-naphth-1-yl-methane 7. (4-Methoxyphenyl)-(4-(2-hydroxy-3-n-butylamino-propoxy)phenyl)-1,2,3,4-tetrahydronaphth-1-yl-methane In an embodiment of the present invention, the catalyst used for Friedel-Crafts reaction is such as $AlCl_3$, $SnCl_4$, or $(CH_3)_3SiCl$.

In another embodiment of the present invention, the solvent used for Friedel-Crafts reaction is hydrocarbon solvents such as benzene, toluene, hexane or pentane.

In another embodiment of the present invention, the reaction is effected at a temperature in the range of $-20°$ C. to $100°$ C. for a period in the range of 1 to 10 hr.

In still another embodiment of the present invention, the catalyst used for hydrogenation is such as Raney Ni, Pd/C, or $Pt_2O$.

In yet another embodiment of the present invention, the hydrogenation is effected at a pressure in the range of 30 to 60 psi at a temperature in the range of $25°$ to $60°$ C. in presence of solvent such as methanol, ethanol, or THF.

In yet another embodiment of the present invention the alkylation is carried out neat or in a non polar solvent, such as acetone, DMSO, in the presence of a base such as $K_2CO_3$, NaOH, KOH, or organic base.

In yet another embodiment of the present invention, the amine used is such as primary or secondary amine containing carbon atoms 2 to 6.

In yet another embodiment of the present invention, the reaction is step (iv) in carried out neat (without solvent) or in presence of polar solvent such as methanol, ethanol, or THF.

In yet another embodiment of the present invention, the salts of formula 1 include hydrochloride, tartrates, citrate, or succinate.

In yet, another embodiment of the present invention, the pharmaceutical composition comprises a compound of formula 1 in an appropriate amount in admixture with a pharmaceutical carrier or a diluent.

In yet another embodiment of the present invention, the compound is used for the prevention and treatment of estrogen related disease or syndromes.

EXAMPLES

Example 1

(4-Methoxyphenyl)-(4-hydroxyphenyl)-naphth-1-yl-methane

A solution of compound (4-methoxyphenyl)-naphth-1-yl-carbinol of formula II (3.0 gm, 0.011 mol) and phenol (5.4 gm, 0.057 mol) in a mixture of anhydrous benzene and anhydrous hexane (40.0 ml), 1:1) was gradually added to a mixture of phenol (1.5 gm, 0.061 mol) and anhydrous aluminum chloride (1.5 gm, 0.011 mol) at $0°$ C. under stirring. After the addition was over, the stirring was continued at room temperature for 3 hrs, the reaction was decomposed by adding crushed ice with conc. HCl (0.5 ml) and extracted with ethyl acetate. The organic layer was washed with water, 5% NaOH, dried over sodium sulphate and concentrated to give an oil which was chromatographed over silica gel to yield the title compound of formula I. Yield 2.3 gm (59.3%).

Example 2

(4-Methoxyphenyl)-(3-methyl-4-hydroxyphenyl)-naphth-1-yl-methane

To a stirred solution of (4-methoxyphenyl)-naphth-1-yl carbinol of formula II (5.0 gm, 0.018 mol )and o-cresol (2.4 ml, 0.022 mol) in a mixture of anhydrous benzene, anhydrous pentane (50 ml, 1:1), and $AlCl_3$ (2.5 gm) was gradually added, after addition stirring was continued for 5–6 hrs at $0–4°$ C. The reaction mixture was decomposed by adding crushed ice with conc. HCl (0.5 ml) and extracted with ethyl acetate. The organic layer was washed successively with water, dried over $Na_2SO_4$ and concentrated to give an oil, which was chromatographed over silica gel using benzene-hexane as the eluent to give the title compound of formula III, yield 4.5 gm (67.16%).

Example 3

(4-Methoxyphenyl)-(4-pyrrolidinoethoxyphenyl)-naphth-1-yl-methane Hydrochloride

A mixture of (4-methoxyphenyl)-(4-hydroxyphenyl)-naphth-1-yl-methane of formula 1 (2.3 gm, 0.007 mol), anhydrous $K_2CO_3$ (4.43 gm), 1-(2-chloroethyl)pyrrolidine hydrochloride (3.0 gm, 0.018 mol) and anhydrous acetone (200 ml), was refluxed for 8–10 hrs, $K_2CO_3$ was filtered off, acetone was distilled off and the residue was diluted with water. The reaction mixture was extracted with ethyl acetate washed with water, dried over $Na_2SO_4$ and concentrated to give an oil. This oil was passed through basic alumina using benzene as eluent. Solvent was distilled off. The oil thus obtained was treated with ethanolic HCl. The solvent was evaporated and compound was crystallized with absolute alcohol and anhydrous ether to give title compound as a salt of general formula I. Yield 0.75 gm(66%).

Example 4

(4-Methoxyphenyl)-(3-methyl-4-pyrrolidinoethoxyphenyl)-naphth-1-yl-methane Hydrochloride A mixture of (4-methoxyphenyl)-(3-methyl-4-hydroxyphenyl)-naphth-1-yl-methane (0.3 gm, 0.008 mol), anhydrous $K_2CO_3$ (2.0 gm), 1-(2-chloroethyl)pyrrolidine hydrochloride (0.3 gm, 0.0017 mol) and anhydrous acetone (25 ml) was refluxed for 10 hrs, $K_2CO_3$ was filtered off, acetone was distilled off, and the residue was diluted with water. The reaction mixture was extracted with ethyl acetate washed with water, dried over $Na_2SO_4$ and concentrated to give an oil. This oil was passed through basic alumina using benzene as eluent. Solvent was distilled off. The oil thus obtained was treated with ethanolic HCl. The solvent was evaporated and compound was crystallized with absolute alcohol and anhydrous ether to give the title compound as a salt of general formula I. Yield 170 mg(46%).

Example 5

(4-Methoxyphenyl)-(4-piperidinoethoxyphenyl)-1-naphth-1-yl-methane

A mixture of (4-methoxyphenyl)-(4-hydroxyphenyl)-naphth-1-yl-methane of formula 1 (0.3 gm, 0.001 mol), anhydrous $K_2CO_3$ (1.5 gm), 1-(2-chloroethyl)piperidine hydrochloride (0.276 gm, 0.002 mol) and dry acetone (100 ml) was refluxed for 810 hrs $K_2CO_3$ was filtered off, acetone was distilled off, and the residue was diluted with water. The reaction mixture was extracted with ethyl acetate washed with water dried over $Na_2SO_4$ and concentrated to give an oil. This oil was purified by column chromatography over basic alumina using benzene as the eluent. Solvent was distilled off to give the title compound of general formula I as an oil. Yield 0.3 gm(67%).

Example 6

(4-Methoxyphenyl)-(4-(2,3-epoxypropyloxy) phenyl)-1-naphth-1-yl-methane

A mixture of (4-methoxyphenyl)-(4-hydroxyphenyl)-1-naphth-1-yl methane of formula I (2.6 g, 0.29 mmol) anhydrous $K_2CO_3$ (2.8 gm, 1.44 mmol), epichlorohydrin (20 ml) was refluxed at 100° C. for 10 hrs. The reaction mixture was filtered and the filtrate was concentrated. The residue was dissolved in ether washed with aq. NaOH (10%) and then with water to neutral, dried over sodium sulphate and the solvent was distilled off. The oil was chromatographed over silica gel. The epoxide was eluted with 20% hexane chloroform to give pure title epoxide of formula I as an oil, yield 1.98 gm (65.38%).

Example 7

(4-Methoxyphenyl)-(3-methyl-4-(2,3-epoxypropyloxy)phenyl)-1-naphth-1-yl-methane

A mixture of (4-methoxyphenyl)-(3-methyl-4-hydroxyphenyl)-1-naphth-1-yl methane (1.0 gm, 0.002 mol), epichlorohydrin (25 ml) and anhydrous $K_2CO_3$ (4.0 gm) was refluxed at 120° C. for 8 hrs. $K_2CO_3$ was filtered off and filtrate was concentrated. The residue obtained was dissolved in ethyl acetate, washed with water, dried over sodium sulphate and concentrated to give an oil which was chromatographed over silica gel using hexane-chloroform as the eluent to give the title compound of general formula I, yield 75 gm (66%).

Example 8

(4-Methoxyphenyl)-(4-(2-hydroxy-3-n-butylaminopropoxy)phenyl-naphth-1-yl-methane, Hydrochloride A mixture of (4-methoxyphenyl)-(4-(2,3-epoxypropyloxypheny))-1-naphth-1-yl methane (3.96 gm, 0.01 mol), n-butyl amine (1 gm, 0.014 mol) and ethanol (10 ml) was refluxed for 6 hrs. Ethanol was distilled off and the residue was passed through basic alumina using benzene-hexane as eluent. The solvent was distilled off yielding the free base compound of formula II as an oil. The oil thus obtained was treated with ethanolic HCl. The solvent was evaporated and compound was crystallized with absolute alcohol and anhydrous ether to give the compound of general formula II as a hydrochloride salt.

Example 9

(4-Methoxyphenyl)-(3-methyl-4-2-hydroxy-3-n-butylamino)propoxy)phenyl)-naphth-1-yl-methane, Hydrochloride A mixture of (4-methoxyphenyl)-(3-methyl-4-(2,3-epoxypropyloxy)phenyl)-1-naphth-1-yl methane of formula I (0.5 gm, 0.001 mol), n-butyl amine (1.0 ml. 0.014 mol) and ethanol was refluxed for 6 hrs. Ethanol was distilled off and the residue was passed through basic alumina column using hexane-ethyl acetate as the eluent. Solvent was distilled off. The oil thus obtained was treated with ethanolic HCl. The solvent was evaporated and the title compound of formula II was obtained as a salt and was crystallized with absolute alcohol and anhydrous ether. Yield 0.25 gm (41.26%).

Example 10

(4-Methoxyphenyl)-(4-hydroxyphenyl)-1,2,3,4-tetrahydro-napth-1-yl-methane

A mixture of (4-methoxyphenyl)-(4-hydroxyphenyl)-naphthyl-1-yl-methane (3.0 gm, 0.008 mol) in methanol (25 ml) and (3.0 gm) of Raney Ni was hydrogenated at 60 psi pressure for 8 hrs. Then the catalyst was filtered off and solvent was distilled off. This crude product was purified on silica gel (flash) by using hexane and ethyl acetate as the eluent to give the compound of formula I. Yield 0.9 gm (29%).

Example 11

(4-Methoxyphenyl)-(4-hydroxyphenyl)-5,6,7,8-tetrahydro-napth-1-yl-methane

A mixture of of (4-methoxyphenyl)(4-hydroxyphenyl) naphthyl-1-yl-methane (30 gm, 0.008 mol) in methanol (25 ml) and (30 gm) of Raney Ni was hydrogenated at 60 psi pressure for 8 hrs. Then catalyst was filtered off and solvent was distilled off. This crude product was purified or, silica gel (flash) by using hexane and ethyl acetate as eluent to give title compound for formula I Yield 8 gm (26%).

Example 12

(4-Methoxyphenyl)-3-methyl-4-hydroxyphenyl)-1,2,3,4-tetrahydro-naphth-1-yl-methane A mixture of (4-methoxyphenyl)(3-methyl-4-hydroxyphenyl-naphth-1-yl-methane (3.8 gm 0.010 mol) in methanol (25 ml) and (3.0 gm) of Raney Ni was hydrogenated at 60 psi pressure for 8 hrs. Then catalyst was filtered off and solvent was distilled off. This crude product was purified on silica gel (flash) with hexane and ethyl acetate as the eluent to give the compound of formula I. Yield 1.2 gm (31.5%).

Example 13

(4-Methoxyphenyl)-(3-methyl-4-hydroxyphenyl)-5,6,7,8-tetrahydro-naphth-1-yl-methane A mixture of (4-methoxyphenyl)(3-methyl-4-hydroxyphenyl)naphthyl-1-yl-methane in (3.8 gm, 0.010 mol) of methanol (25 ml) and (3.0 gm) of Raney Ni was hydrogenated at 60 psi pressure for 9 hrs. Then catalyst was filtered off and solvent was distilled off. This crude product was purified on silica gel (flash) with hexane and ethyl acetate as the eluent to give the title compound of formula I. Yield 0.6 gm (15.78%).

Example 14

(4-Methoxyphenyl)(4-pyrrolidinoethoxyphenyl)-1,2,3,4-tetrahydro-naphth-1-yl-methane Hydrochloride A mixture of (4-methoxyphenyl)-(4-hydroxyphenyl)-1,2,3,4-tetrahydronaphth-1-yl-methane (400 mg, 0.001 mol), anhydrous $K_2CO3$ (2.0 gm, 0.14 mol), 1-(2-chloroethyl) pyrrolidine hydrochloride (400 mg, 0.002) and dry acetone (25.0 ml) was refluxed for 10 hrs. $K_2CO_3$ was filtered off, acetone was distilled off and the residue was diluted with water. The reaction mixture was extracted with ethyl acetate, washed with water, dried over sodium sulphate and concentrated to give an oil which was filtered through basic alumina column using benzene as the eluent, and concentrated to give an oil. The oil thus obtained was treated with ethanolic HCl. The solvent was evaporated and the compound was crystallized with absolute alcohol and dry ether, filtered under anhydrous conditions, and dried to give the title compound of formula I. Yield 350 mg. (68.35%).

Example 15

(4-Methoxyphenyl)-(3-methyl-4-pyrrolidinoethoxy-phenyl)-1,2,3,4-tetrahydro-naphth-1-yl-methane Hydrochloride A mixture of (4-methoxyphenyl)-(3-methyl-4-hydroxyphenyl)-1,2,3,4-tetrahydronaphthyl-1-yl-methane (322 mg, 0.009 mol), anhydrous. $K_2CO_3$ (2.0 gm, 0.14 mol), 1-(2-chloroethyl)pyrrolidine hydrochloride (300 mg, 0.0017) and dry acetone (25.0 ml) was refluxed for 10 hrs, $K_2CO_3$ was filtered off, acetone was distilled off and the residue was diluted with water. The reaction mixture was extracted with ethyl acetate, washed with water, dried over sodium sulphate and concentrated to give an oil which was filtered through basic alumina column by using benzene as eluent, and concentrated. The oil thus obtained was treated with ethanolic HCl. The solvent was evaporated and the compound was crystallized with absolute alcohol and dry ether, and filtered under anhydrous conditions to give title compound of formula I. Yield 190 mg. (44%).

Example 16

(4-Methoxyphenyl)-(4-pyrrolidinoethoxy-phenyl)-1,2,3,4-tetrahydro-naphth-1-yl-methane A mixture of (4-methoxyphenyl)-(4-hydroxyphenyl)-1,2,3,4-tetrahydronaphth-1-yl-methane (400 mg 0.0011 mol), anhydrous $K_2CO_3$ (2.0 gm, 0.014 mol), 1-(2-chloroethyl) piperidine hydrochloride (400 mg, 0.002) and dry acetone (25.0 ml) was refluxed for 10 hrs, $K_2CO_3$ was filtered off acetone was distilled off and residue was diluted with water. The reaction mixture was extracted with ethyl acetate, washed with water, dried over sodium sulphate and concentrated to give an oil which was filtered through basic alumina column by using benzene as eluent, and was concentrated. The oil thus obtained was treated with ethanolic HCl. The solvent was evaporated and compound was crystallized with absolute alcohol and anhydrous ether, and filtered under anhydrous conditions to give title compound of formula I. Yield 310 mg. (58.6%).

Example 17

(4-Methoxyphenyl)-(3-methyl-4-pyrrolidinoethoxy-phenyl)-1,2,3,4-tetrahydro-naphth-1-yl-methane A mixture of (4-methoxyphenyl)(3-methyl-4-hydroxyphenyl)-1,2,3,4-tetrahydronaphth-1-yl-methane (345 mg, 0.001 mol), anhydrous $K_2CO_3$ (2.0 gm, 0.014 mol), and 1-(2-chloroethyl)piperidine hydrochloride (400 mg, 0.002 ml) and dry acetone (25.0 ml) was refluxed for 10 hrs, $K_2CO_3$ was filtered off, acetone was distilled off, and the residue was diluted with water. The reaction mixture was extracted with ethyl acetate, washed with water, dried over sodium sulphate and concentrated to give an oil which was filtered through basic alumina column with benzene as the eluent and concentrated to give title compound of formula I. Yield 324 mg (72%).

Example 18

(4-Methoxyphenyl))-(4-pyrrolidinoethoxy-phenyl)-5,6,7,8-tetrahydro-naphth-1-yl-methane Hydrochloride A mixture of (4-methoxyphenyl)-(4-hydroxyphenyl)-5,6,7,8-tetrahydronaphth-1-yl-methane (300 mg, 0.001 mol), anhydrous $K_2CO_3$ (2.0 gm, 0.014 mol), 1-(2-chloroethyl) pyrrolidine hydrochloride (400 mg, 0.002 mol) and dry acetone (25.0 ml) was refluxed for 10 hrs, $K_2CO_3$ was filtered off, acetone was distilled off and residue was diluted with water. The reaction mixture was extracted with ethyl acetate, washed with water, dried over sodium sulphate and concentrated to give an oil which was filtered through basic alumina column with benzene as the eluent. The oil thus obtained was treated with ethanolic HCl. The solvent was evaporated and compound was crystallized with absolute alcohol and anhydrous ether filtered under anhydrous condition to give title compound of formula I. Yield 176 mg (42.30%).

Example 19

(4-Methoxyphenyl}-(3-methyl-4-pyrrolidinoethoxy-phenyl)-5,6,7,8-tetrahydro-napth-1-yl-methane Hydrochloride A mixture of (4-methoxyphenyl)-(3-methyl-4-hydroxyphenyl)-5,6,7,8-tetrahydronaphthyl-1-yl-methane (330 mg, 0.001 mol), anhydrous $K_2CO_3$ (2.0 gm, 0.14 mol), 1-(2-chloroethyl(pyrrolidine hydrochloride (400 mg, 0.002 mol) and dry acetone (25.0 ml) was refluxed for 10 hrs $K_2CO_3$ was filtered off, acetone was distilled off and the residue was diluted with water. The reaction mixture was extracted with ethyl acetate, washed with water dried over sodium sulphate and concentrated to give an oil which was filtered through basic alumina column using benzene as eluent. The oil thus obtained was treated with ethanolic HCl. The solvent was evaporated and compound was crystallized with absolute alcohol and anhydrous ether, and filtered under anhydrous conditions to give the title compound of formula I. Yield 220 mg. (48 5%).

Example 20

(4-Methoxyphenyl)-(4-pyrrolidinoethoxy-phenyl)-5,6,7,8-tetrahydro-napth-1-yl-methane A mixture of (4-methoxyphenyl)-(4-hydroxyphenyl)-5,6,7,8-tetrahydronaphth-1-yl-methane (300 mg, 0.001 mol), anhydrous $K_2CO_3$ (2.0 gm, 0.014 mol), 1-(2-chloroethyl) piperidine hydrochloride (300 mg, 0.0015 mol) and dry acetone (25.0 ml) was refluxed for 10 hrs, $K_2CO_3$ was filtered off, acetone was distilled off and residue was diluted with water. The reaction mixture was extracted with ethyl acetate, washed with water, dried over sodium sulphate and concentrated to give an oil which was filtered through basic alumina column with benzene as the eluent and concentrated to give the title compound of formula I. Yield 218 mg. (55.89%).

Example 21

(4-Methoxyphenyl)-(3-methyl-4-pyrrolidinoethoxy-phenyl)-5,6,7,8-tetrahydro-naphth-1-yl-methane A mixture of (4-methoxyphenyl)-(3-methyl-4-hydroxy-phenyl)-5,6,7,8-tetrahydro-naphth-1-yl-methane (330 mg, 0.001 mol), anhydrous. $K_2CO_3$ (2.0 gm, 0.14 mol), 1-(2-chloroethyl)piperidine hydrochloride (400 mg, 0.002 mol) and dry acetone (25.0 ml) was refluxed for 10 hrs, $K_2CO_3$ was filtered off, acetone was distilled off and the residue was diluted with water. The reaction mixture was extracted with ethyl acetate, washed with water, dried over sodium sulphate and concentrated to give an oil which was filtered through basic alumina column with benzene as the eluent to give the title compound of formula I. Yield 210 mg. (7.19%).

Example 22

(4-Methoxyphenyl)-(4-(2,3-epoxy-propyloxy (phenyl-1,2,3,4-tetrahydro-naphth-1-yl-methane A mixture of (4-methoxyphenyl}-(4-hydroxyphenyl)-1,2,3,4-tetrahydronaphth-1-yl-methane (1.0 gm, 0.29 mmol), anhydrous $K_2CO_3$ (4.0 gm, 0.28 mol), epichlorohydrin (20 ml) was refluxed at 100–120° C. for 8 hrs. The reaction mixture was filtered and the filtrate was concentrated. The residue was dissolved in ethyl acetate, washed with water, dried over sodium sulphate and concentrated to give an oil. The oil was chromatographed over silica gel, to give the title compound. Yield 1.1 gm, 94.8%).

Example 23

(4-Methoxyphenyl)-(3-methyl-4-(2,3-epoxypropyloxy-phenyl)-1,2,3,4-tetrahydro-1-naphth-1-yl-methane A mixture of (4-methoxyphenyl)-(3-methyl-4-hydroxyphenyl)-1,2,3,4-tetrahydronaphth-1-yl-methane (600 mg, 0.002 mol), epichlorohydrin (25 ml) and anhydrous $K_3CO_3$ (4.0 gm. 0.028 mol) was refluxed at 120° C. for 8 hrs. $K_2CO_3$ was filtered off and the filtrate was concentrated. The residue obtained was dissolved in ethyl acetate and washed with water, dried over sodium sulphate and concentrated to give the title compound as an oil. Yield 610 mg (88.4%).

Example 24

(4-Methoxyphenyl)-(4-(2-hydroxy-3-di-butylamino-propoxy-phenyl)-1,2,3,4-tetrahydro-naphth-1-yl-methane A mixture of (4-methoxyphenyl)-(4-(2,3-epoxy-propyloxy)phenyl)-1,2,3,4-tetrahydro-naphth-1-yl-methane (300 mg, 0.001 mol), dibutyl amine (1.0 ml) and ethanol (10 ml) was refluxed for 12 hrs. Ethanol was distilled off and the residue was passed through basic alumina using benzene-:ethyl acetate as the eluent. The solvent was distilled off yielding the required product. Yield 192 mg (49.23%).

Example 25

(4-Methoxyphenyl)-(4-(2-hydroxy-3-n-butylaminopropoxy)phenyl)-1,2,3,4-tetrahydro-naphth-1-yl-methane A mixture of (4-methoxyphenyl)-(4-(2,3-epoxypropyloxy)phenyl)-1,2,3,4-tetrahydronaphth-1-yl-methane (400 mg, 0.01 mol), n-butyl amine (1.0 ml, 0.01 mol) and ethanol (10 ml) was refluxed for 8 hrs. Ethanol was distilled off and the residue was passed through basic alumina using benzene:ethyl acetate as the eluent. The solvent was distilled off yielding the required product. Yield 230 mg (48.93%).

Example 26

(4-Methoxyphenyl)-(3-methyl-4-(2-hydroxy-3-n-butylaminopropoxy)phenyl)-1,2,3,4-tetrahydro-naphth-1-yl-methane A mixture of (4-methoxyphenyl)-(3-methyl-4-(2,3-epoxypropyloxy)phenyl)-1,2,3,4-tetrahydronaphth-1-yl-methane (300 mg, 0.001 mol), n-butyl amine (1.0 m, 0.01 mol) and ethanol (15 ml) was refluxed for 8 hrs. Ethanol was distilled off and the residue was passed through a basic alumina column using hexane:ethyl acetate as the eluent. Solvent was distilled off to give the title compound. Yield 212 mg, (60.05%).

Example 27

(4-Methoxyphenyl)-(4-(2,3-epoxy-propyloxy) phenyl)-5,6,7,8-tetrahydronaphth-1-yl-methane A mixture of (4-methoxyphenyl)-(4-hydroxyphenyl)-5,6,7,8-tetrahydronaphth-1-yl-methane (450 mg, 0.0013 mol) anhydrous $K_2CO_3$ (2.8 gm, 1.44 mmol), epichlorohydrin (20 ml) was refluxed at 100–120° C. for 12 hrs. The reaction mixture was filtered and the filtrate was concentrated. The residue was dissolved in ethyl acetate, washed with water, dried over sodium sulphate and concentrated to give an oil. The oil was chromatographed over silica gel using 20% hexane:chloroform as the eluent to give the desired compound as an oil. Yield 410 mg (78.39%).

Example 28

(4-Methoxyphenyl)-(4-(2,3-epoxy-propyloxy) phenyl)-5,6,7,8-tetrahydronaphth-1-yl-methane A mixture of (4-methoxyphenyl)-(3-methyl-4-hydroxyphenyl)-5,6,7,8-tetrahydronaphth-1-yl-methane (410 mg, 0.001 mol), epichlorohydrin (25 ml) and anhydrous $K_2CO_3$ (2.0 gm, 0.014 mol) was refluxed at 120° C. for 6 hrs, $K_2CO_3$ was filtered off and the filtrate was concentrated. The residue obtained was dissolved in ethyl acetate and washed with water, dried over sodium sulphate and concentrated to give an oil which was chromatographed over silica gel using hexane:chloroform as the eluent to give the title compound. Yield 388 mg (82.37%).

Example 29

(4-methoxyphenyl)-4-(2-hydroxy-3-n-butylaminopropoxy)-phenyl)-5,6,7,8-tetrahydronaphth-1-yl-methane A mixture of (4-methoxyphenyl)-(3-methyl-4-hydroxyphenyl)-5,6,7,8-tetrahydronaphth-1-yl-methane (350 mg, 0.004 mol), n-butyl amine (1.0 ml, 0.01 mol) and ethanol (10 ml) was refluxed for 6 hrs. Ethanol was distilled off and the residue was passed through basic alumina using benzene:ethyl acetate as the eluent. The solvent was distilled off yielding the required product. Yield 286 mg (69.75%).

Example 30

(4-methoxyphenyl)-4-(2-hydroxy-3-n-butylaminopropoxy)-phenyl)-5,6,7,8-tetrahydronaphth-1-yl-methane A mixture of (4-methoxyphenyl)-(3-methyl-4-hydroxyphenyl)-5,6,7,8-tetrahydronaphth-1-yl-methane (380 mg, 0.001 mol); n-butyl amine (1.0 ml, 0.01 mol) and ethanol was refluxed for 6 hrs. Ethanol was distilled off and the residue was passed through a basic alumina using hexane:ethyl acetate as the eluent. Solvent was distilled off to give the title compound. Yield 236 mg (52.79%).

What is claimed is:

1. A diaryl tetrahydro-naphthyl methane compound or a pharmaceutically acceptable acid addition salt thereof, wherein the diaryl tetrahydro-naphthyl compound is of formula I:

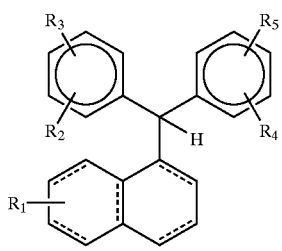

Formula I wherein $R_1$, $R_2$, $R_3$, $R_4$, and $R_5$ are each individually selected from the group consisting of H, OH, lower alkyl, lower alkoxy and substituted lower alkoxy group, wherein the lower alkyl and lower alkyl portion of the lower alkoxy group is a straight or branched chain radical containing 1–6 carbon atoms:

wherein at least one of $R_2$, $R_3$, $R_4$ and $R_5$ is an alkoxy group substituted with at least one selected from the group consisting of hydrogen, hydroxy, epoxy, alkylamino, dialkylamino, cyclic alkyl amino and $N(CH_2)_n$, wherein n=2 to 8; and wherein the dotted lines on the naphthyl rings represent a 1,2,3,4-tetrahydronaphthyl ring or a 5,6,7,8-tetrahydronaphthyl ring.

2. A diaryl naphthyl methane compound or a pharmaceutically acceptable acid addition salt thereof, wherein the diaryl naphthyl compound is of formula I:

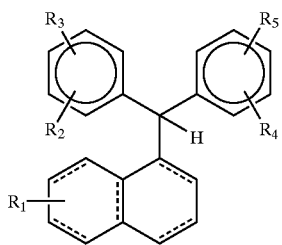

Formula I wherein $R_1$, $R_2$, $R_3$, $R_4$, and $R_5$ are each individually selected from the group consisting of H, OH, lower alkyl, lower alkoxy and substituted lower alkoxy group, wherein the lower alkyl and lower alkyl portion of the lower alkoxy group is a straight or branched chain radical containing 1–6 carbon atoms:

wherein at least one of $R_2$, $R_3$, $R_4$ and $R_5$ is an alkoxy group substituted with at least one selected from the group consisting of hydroxy, amino, alkylamino, dialkylamino and $N(CH_2)_n$, wherein n=2 to 8; and wherein the dotted lines on the naphthyl rings represent a naphthyl ring.

3. The compound according to claim 1, wherein the lower alkyl or the alkyl residue of the lower alkoxy group is at least one selected from the group consisting of methyl, ethyl, n-propyl, isopropyl, n-butyl, tertiary butyl, n-amyl, n-hexyl, and 2-ethyl butyl.

4. The compound according to claim 2, wherein the lower alkyl or the alkyl residue of the lower alkoxy group is at least one selected from the group consisting of methyl, ethyl, n-propyl, isopropyl, n-butyl, tertiary butyl, n-amyl, n-hexyl, and 2-ethyl butyl.

5. The compound or pharmaceutically acceptable acid addition salt thereof as claimed in claim 1 or 2, which are selected from the group consisting of:

(a) (4-methoxyphenyl)-(4-pyrrolidinoethoxyphenyl)-naphth-1-yl-methane hydrochloride, (b) (4-methoxyphenyl)-(4-piperidinoethoxyphenyl)-naphth-1-yl-methane, (c) (4-methoxyphenyl)-(4-piperidinoethoxyphenyl)-1,2,3,4-tetrahydro-naphth-1-yl-methane, (d) (4-methoxyphenyl)-(3-methyl-4-piperidinoethoxyphenyl)-1,2,3,4-tetrahydro-naphth-1-yl-methane, (e) (4-methoxyphenyl)-(4-(2-hydroxy-3n-dibutylaminopropoxy)phenyl)-1,2,3,4-tetrahydro-naphth-1-yl-methane, (f) (4-methoxyphenyl)-(4-pyrrolidinoethoxyphenyl)-5,6,7,8-tetrahydro-naphth-1-yl-methane HCl, (g) (4-methoxyphenyl)-(4-N,N-diethylamino-ethoxyphenyl)-5,6,7,8-tetrahydro-naphth-1-yl-methane, (h) (4-methoxyphenyl)-(4-piperidinoethoxyphenyl)-naphth-1-yl-methane hydrochloride, (i) (4-methoxyphenyl)-(4-piperidinoethoxyphenyl)-naphth-1-yl-methane, (j) (4-methoxyphenyl)-(3-methyl-4-piperidinoethoxyphenyl)-naphth-1-yl-methane, (k) (4-methoxyphenyl)-(4-pyrrolidinoethoxyphenyl)-1,2,3,4-tetrahydro-naphth-1-yl-methane, (l) (4-methoxyphenyl)-(4-pyrrolidinoethoxyphenyl)-5,6,7,8-tetrahydro-naphth-1-yl-methane hydrochloride, and (m) (4-methoxyphenyl)-(4-(2-hydroxy-3-n-butylaminopropoxy)phenyl)-1,2,3,4-tetrahydro-naphth-1-yl-methane.

6. (4-methoxyphenyl)-(4-(2-hydroxy-3-cyclopropylamino-propoxy)-phenyl)-naphth-1-yl-methane or a pharmaceutically acceptable acid addition salt thereof.

7. A pharmaceutical composition comprising a therapeutically effective amount of compound as claimed in claim 1 or 2 together with a pharmaceutically acceptable carrier or diluent.

8. The pharmaceutical composition as claimed in claim 7, wherein the carrier is at least one selected from the group consisting of water, corn starch, potato starch, salt solution, alcohol, polyethylene glycol, polyhydroxyethoxylated caster oil, gelatin, lactose, amylase, magnesium stearate, talc, silicic acid, fatty acid, monoglycerides, diglycerides, pentaerythritol fatty acid esters, hydroxymethyl cellulose and polyvinylpyrrolidene.

9. The pharmaceutical composition as claimed in claim 7 wherein the diluent is at least one selected from the group consisting of wetting agent, emulsifying agent, suspending agent, preserving agent, sweetening agent and flavouring agent.

10. The pharmaceutical composition as claimed in claim 7 wherein the composition is in a tablet, injection or syrup.

11. A method of treating a patient suffering from breast cancer, osteoporosis, hypocholesteremia or endometriosis comprising administering a therapeutically effective amount of the compound of claim 1 or 2.

12. A process for preparing a compound as claimed in claim 1 or 2 comprising:

(a) subjecting α-naphthoic acid or a substituted α-naphthoic acid to a Friedel Crafts reaction with a substituted phenolic compound in a hydrocarbon solvent and a Lewis acid in the temperature range of −20° C. to 100° C. for a period of 1–10 hours to yield a naphthophenone derivative, (b) subjecting the naphthophenone derivative to hydrogenation with a suitable catalyst in a solvent to obtain a diaryl naphthyl carbinol derivative wherein the suitable catalyst of step (b) is at least one selected from the group consisting of metal hydride, Raney nickel, palladium charcoal (Pd/C), and platinum oxide, and wherein the solvent of step (b) is at least one selected from the group consisting of a protic solvent and THF, (c) subjecting the product of step (b) to Friedel Crafts reaction with phenol to obtain corresponding naphthyl diaryl methane derivative having at least one free phenolic hydroxyl group, and (d) treating the compound of step (c) with a tertiary amino alkyl halide to obtain a tertiary amino alkoxy compound or with an epoxy alkyl halide under basic conditions to obtain the corresponding epoxy alkoxy compound, which is further treated with a suitable primary amine to obtain a hydroxy substituted secondary amino alkoxy compound of formula (Ia), or (e) hydrogenating the compound of step (c) in the presence of a suitable catalyst to obtain a tetrahydronaphthyl diaryl methane derivative and subjecting the tetrahydronaphthyl diaryl methane derivative to the process of step (d) to obtain a compound of formula (I), (f) optionally treating the compound of step (d) or (e) with an inorganic or organic acid to obtain the corresponding salt.

13. The process as claimed in claim 12, wherein α-naphthoic acid is subjected to the Friedal Crafts reaction.

14. The process as claimed in claim 12, wherein in step (a), the Lewis acid is at least one selected from the group consisting of $AlCl_3$, $SnCl_4$ and $(CH_3)_3SiCl$.

15. The process as claimed in claim 12, wherein in step (a), the hydrocarbon solvent is at least one selected from the group consisting of benzene, toluene, pentane and hexane.

16. The process as claimed in claim 12, wherein the hydrogenation reaction of step (e) is performed and the hydrogenation is effected at a pressure in the range of 30 to 60 psi and at a temperature ranging from 25° C. to 60° C.

17. The process as claimed in claim 12, wherein in the hydrogenation reaction of step (e), the suitable catalyst is at least one selected from the group consisting of Raney nickel, palladium charcoal (Pd/C) and platinum oxide ($PtO_2$).

18. The process as claimed in claim 12, wherein in the hydrogenation reaction of step (e), the solvent is at least one selected from the group consisting of methanol, ethanol and tetrahydrofuran.

19. The process as claimed in claim 12, wherein the tertiary amino alkyl halide is at least one selected from the group consisting of $ClCH_2CH_2HN$-cyclopropyl, 2-chloro-n-butyl amine, N-chloromethylpiperidine, N-chloromethyl pyrrolidine, and chloroethyl dimethylamine, and wherein the epoxy alkyl halide is epichlorohydrin.

20. The process as claimed in claim 12, wherein in step (d), the base is at least one selected from the group consisting of $K_2CO_3$, NaOH and KOH.

21. The process as claimed in claim 12, wherein in step (d), the solvent is at least one selected from the group consisting of acetone and dimethyl sulfoxide.

22. The process as claimed in claim 12, wherein in step (d), the amine is at least one selected from the group consisting of a substituted or unsubstituted straight chain or cyclic aliphatic, aromatic and heterocyclic amines.

23. The process as claimed in claim 12, wherein in step (f), the acid is at least one selected from the group consisting of hydrochloric acid, tartaric acid, citric acid and succinic acid.

* * * * *

UNITED STATES PATENT AND TRADEMARK OFFICE
CERTIFICATE OF CORRECTION

PATENT NO. : 6,610,705 B1
DATED : August 26, 2003
INVENTOR(S) : Srivastava et al.

It is certified that error appears in the above-identified patent and that said Letters Patent is hereby corrected as shown below:

<u>Title page,</u>
Item [75], Inventors, should read:
-- Neeta Srivastava, Lucknow-1 (IN);
Arvinder Grover, Lucknow-1 (IN);
Sangita (Full name as Shown), Lucknow-1 (IN);
Atul Kumar, Lucknow-1 (IN);
Man Mohan Singh, Lucknow-1 (IN);
Janak Dulari Dhar, Lucknow-1 (IN);
Suprabhat Ray, Lucknow (IN) --

Signed and Sealed this

Sixth Day of July, 2004

JON W. DUDAS
*Acting Director of the United States Patent and Trademark Office*